(12) United States Patent
Thakur et al.

(10) Patent No.: US 9,144,391 B2
(45) Date of Patent: Sep. 29, 2015

(54) ENHANCED ACTIVATION ONSET TIME OPTIMIZATION BY SIMILARITY BASED PATTERN MATCHING

(71) Applicant: Boston Scientific Scimed Inc., Maple Grove, MN (US)

(72) Inventors: Pramodsingh H. Thakur, White Bear Lake, MN (US); Shantha Arcot-Krishnamurthy, Vadnais-Heights, MN (US); Allan C. Shuros, St. Paul, MN (US); Shibaji Shome, Arden Hills, MN (US); Barun Maskara, Blaine, MN (US); Sunipa Saha, Shoreview, MN (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 14/279,723

(22) Filed: May 16, 2014

(65) Prior Publication Data
US 2014/0343442 A1    Nov. 20, 2014

Related U.S. Application Data

(60) Provisional application No. 61/824,245, filed on May 16, 2013.

(51) Int. Cl.
*A61B 5/0452* (2006.01)
*A61B 5/042* (2006.01)
*A61B 5/00* (2006.01)
*A61B 5/046* (2006.01)
*A61B 18/14* (2006.01)

(52) U.S. Cl.
CPC .......... *A61B 5/04525* (2013.01); *A61B 5/0422* (2013.01); *A61B 5/7246* (2013.01); *A61B 5/046* (2013.01); *A61B 5/6858* (2013.01); *A61B 18/1492* (2013.01)

(58) Field of Classification Search
None
See application file for complete search history.

(56) References Cited

U.S. PATENT DOCUMENTS

| | | | |
|---|---|---|---|
| 5,647,870 | A | 7/1997 | Kordis et al. |
| 6,070,094 | A | 5/2000 | Swanson et al. |
| 6,233,491 | B1 | 5/2001 | Kordis et al. |
| 6,574,492 | B1 | 6/2003 | Ben-Haim et al. |
| 6,600,948 | B2 | 7/2003 | Ben-Haim et al. |
| 6,735,465 | B2 | 5/2004 | Panescu |
| 6,950,689 | B1 | 9/2005 | Willis et al. |
| 7,841,986 | B2 | 11/2010 | He et al. |
| 2011/0251505 | A1 | 10/2011 | Narayan et al. |

OTHER PUBLICATIONS

Houben, Richard P.M. et al., "Processing Intracardiac Electrograms in Atrial Fibrillation", Diagosis of Electropathological Substrate of AF, IEEE Engineering in Medicine and Biology Magazine, Nov./Dec. 2006, pp. 40-51.
International Search Report and Written Opinion issued in PCT/US2014/038357, mailed Sep. 1, 2014, 11 pages.

*Primary Examiner* — Brian T Gedeon
(74) *Attorney, Agent, or Firm* — Faegre Baker Daniels LLP

(57) ABSTRACT

An anatomical mapping system and method includes mapping electrodes configured to detect activation signals of cardiac activity. A processing system is configured to record the detected activation signals and generate a vector field for each sensed activation signal during each instance of the physiological activity. The processing system determines an onset time and alternative onset time candidates, identifies an initial vector field template based on a degree of similarity between the initial vector field and a vector field template from a bank of templates, then determines an optimized onset time for each activation signal based on a degree similarity between the onset time candidates and initial vector field template.

20 Claims, 5 Drawing Sheets

ENHANCED ACTIVATION ONSET TIME OPTIMIZATION BY SIMILARITY BASED PATTERN MATCHING

CROSS-REFERENCE TO RELATED APPLICATION

This application claims priority to Provisional Application No. 61/824,245, filed May 16, 2013, which is herein incorporated by reference in its entirety.

TECHNICAL FIELD

The present invention relates to medical devices and methods for accessing an anatomical space of the body. More specifically, the invention relates to devices and methods for generating vector field maps of electrical activity of anatomical structures.

BACKGROUND

Diagnosing and treating heart rhythm disorders often involve the introduction of a catheter having a plurality of sensors/probes into a cardiac chamber through the surrounding vasculature. The sensors detect electric activity of the heart at sensor locations in the heart. The electric activity is generally processed into electrogram signals that represent signal propagation through cardiac tissue at the sensor locations.

Systems can be configured to display the electrical signals detected in the cardiac chamber as an activation map based on voltages detected. Robust and reliable estimation of onset times for sensed activation signals is the key to visualizing underlying activation patterns and identify targets for applying therapy, e.g. ablation therapy. Traditional methods use characteristic features of the activation signals such as steepest descent for a unipolar signal or most negative peak of a derivative unipolar signal. Any characteristic feature is susceptible to ambiguity stemming from noise or other artifacts, such as a far-field activation signal or multiple large negative peaks adjacent to one another, which superimpose over the signal of interest. There exists a need to improve the reliability of detection of onset times of activation signals in anatomical mapping.

SUMMARY

In Example 1, a method for mapping an anatomical structure includes sensing activation signals during an instance of physiological activity with a plurality of mapping electrodes disposed in or near the anatomical structure, generating a vector field for each sensed activation signal during each instance of the physiological activity, determining an onset time and alternative onset time candidates for each activation signal, identifying an initial vector field pattern template for each activation signal based on a degree of similarity between the generated vector field and at least one vector field template pattern, and determining an optimized onset time for each activation signal based on the corresponding onset time candidates and the initial vector field pattern template.

In Example 2, the method according to Example 1, further includes replacing the determined onset times with corresponding optimized onset times, and generating a display on a display device of the activation signals based on the optimized onset times.

In Example 3, the method according to either of Examples 1 and 2, wherein determining an onset time further includes calculating a derivative of the sensed activation signals, and identifying a minimum peak for each sensed activation signal.

In Example 4, the method according to any one of Examples 1-3, wherein determining alternative onset time candidates further includes identifying negative peaks among the derivative sensed activation signals which are at least one of within a local neighborhood of an identified minimum peak and within an amplitude threshold based on the amplitude of the corresponding minimum peak.

In Example 5, the method according to any one of Examples 1-4, wherein identifying an initial vector field pattern template further includes determining a degree of similarity between each generated vector field and at least one vector field template pattern of a bank of vector field template patterns, and identifying a vector field template pattern having a maximum degree of similarity with a corresponding vector field.

In Example 6, the method according to any one of Examples 1-5, wherein determining optimized onset times further includes generating a vector field candidate for each onset time candidate, determining a degree of similarity between each vector field candidate and the vector field generated based on the corresponding activation signal, and identifying if the degree of similarity between the vector field candidate and the vector field exceeds the degree of similarity between the vector field and initial vector field pattern.

In Example 7, a method for mapping cardiac tissue includes sensing activation signals of electrical cardiac activity during each heart beat with a plurality of mapping electrodes disposed in or near the heart, generating a vector field for each sensed activation signal during each heart beat, determining an onset time and alternative onset time candidates for each activation signal, identifying an initial vector field pattern template for each activation signal based on a degree of similarity between the generated vector field and at least one vector field template pattern, and determining an optimized onset time for each activation signal based on the corresponding onset time candidates and the initial vector field pattern template.

In Example 8, the method according to Example 7, further includes replacing the determined onset times with corresponding optimized onset times, and generating a display on a display device of the activation signals of the heart based on the optimized onset times.

In Example 9, the method according to either of Examples 7 and 8, wherein determining an onset time further includes calculating a derivative of the sensed activation signals, and identifying a minimum peak for each sensed activation signal.

In Example 10, the method according to any one of Examples 7-9, wherein determining alternative onset time candidates further includes identifying negative peaks among the derivative sensed activation signals which are at least one of within a local neighborhood of an identified minimum peak and within an amplitude threshold based on the amplitude of the corresponding minimum peak.

In Example 11, the method according to any one of Examples 7-10, wherein identifying an initial vector field pattern template further includes determining a degree of similarity between each generated vector field and at least one vector field template pattern of a bank of vector field template patterns, and identifying a vector field template pattern having a maximum degree of similarity with a corresponding vector field.

In Example 12, the method according to any one of Examples 7-11, wherein determining optimized onset times further includes generating a vector field candidate for each onset time candidate, determining a degree of similarity between each vector field candidate and the vector field generated based on the corresponding activation signal, and updating the onset time with a corresponding onset time candidate if the degree of similarity between the vector field candidate and the vector field exceeds the degree of similarity between the vector field and initial vector field pattern.

In Example 13, an anatomical mapping system includes a plurality of mapping electrodes disposed in or near the anatomical structure configured to detect activation signals during an instance of physiological activity, and a processing system associated with the plurality of mapping electrodes, the mapping processor configured to record the detected activation signals and associate one of the plurality of mapping electrodes with each recorded activation signal, the processor system further configured to generate a vector field for each sensed activation signal during each instance of the physiological activity, determine an onset time and alternative onset time candidates for each activation signal, identify an initial vector field pattern template for each activation signal based on a degree of similarity between the generated vector field and at least one vector field template pattern, and determine an optimized onset time for each activation signal based on the corresponding onset time candidates and the initial vector field pattern template.

In Example 14, the anatomical mapping system according to Example 13, wherein the processing system is further configured to replace the determined onset times with corresponding optimized onset times, and generate a display on a display device of the activation signals based on the optimized onset times.

In Example 15, the anatomical mapping system according to either of Examples 13 and 14, wherein, to determine an onset time, the processing system is further configured to calculate a derivative of the sensed activation signals, and identifying a minimum peak for each sensed activation signal.

In Example 16, the anatomical mapping system according to any one of Examples 13-15, wherein, to determine alternative onset time candidates, the processing system is further configured to identify negative peaks among the derivative sensed activation signals which are at least one of within a local neighborhood of an identified minimum peak and within an amplitude threshold based on the amplitude of the corresponding minimum peak.

In Example 17, the anatomical mapping system according to any one of Examples 13-16, wherein, to identify an initial vector field pattern template, the processing system is further configured to determine a degree of similarity between each generated vector field and at least one vector field template pattern of a bank of vector field template patterns, and identify a vector field template pattern having a maximum degree of similarity with a corresponding vector field.

In Example 18, the anatomical mapping system according to any one of Examples 13-17, wherein, to determine optimized onset times, the processing system is further configured to generate a vector field candidate for each onset time candidate, determine a degree of similarity between each vector field candidate and the vector field generated based on the corresponding activation signal, and identify if the degree of similarity between the vector field candidate and the vector field exceeds the degree of similarity between the vector field and initial vector field pattern.

In Example 19, a method for mapping an anatomical structure includes sensing activation signals of physiological activity with a plurality of mapping electrodes disposed in or near the anatomical structure, each mapping electrode having an electrode location, determining an onset time and alternative onset time candidates for each activation signal, wherein an onset time indicates an onset of activation signals at a corresponding electrode location during the corresponding instance of the physiological activity, generating an initial characteristic representation of the sensed activation signals based on the determined onset times during the corresponding instance of physiological activity, determining an initial pattern for each initial characteristic representation, the initial pattern representing a characteristic propagation pattern of the activations signals during the corresponding instance of the physiological activity, generating a candidate characteristic representation of the sensed activation signal based each of the corresponding alternative onset time candidates, and determining an optimized onset time for each activation signal based on the candidate characteristic representations and the initial pattern.

In Example 20, the method according to Example 19, further includes replacing the determined onset times with corresponding optimized onset times, and generating a display of the activation pattern on a display device based on the optimized onset times.

In Example 21, the method according to either of Examples 19 and 20, wherein determining an onset time further includes calculating a derivative of the sensed activation signals, and identifying a minimum peak for each sensed activation signal.

In Example 22, the method according to any one of Examples 19-21, wherein determining alternative onset time candidates further includes identifying negative peaks among the derivative sensed activation signals which are at least one of within a local neighborhood of an identified minimum peak and within an amplitude threshold based on the amplitude of the corresponding minimum peak.

In Example 23, the method according to any one of Examples 19-22, wherein determining an initial pattern further includes determining a similarity index between the initial characteristic representation and each of a plurality of pattern templates of a bank of pattern templates, and identifying the pattern template which maximizes the degree of similarity to the initial characteristic representation.

In Example 24, the method according to any one of Examples 19-23, wherein and the pattern templates are characteristic representations of expected patterns of propagation across the plurality of electrodes.

In Example 25, the method according to any one of Examples 19-24, wherein generating a candidate characteristic representation further includes replacing an onset time with each corresponding onset time candidate, and generating a characteristic representation based on each onset time candidate.

In Example 26, the method according to any one of Examples 19-25, wherein determining the optimized onset time further includes determining a degree of similarity between each candidate characteristic representation and the initial pattern, and identifying the candidate characteristic representation and corresponding onset time candidate which maximizes the degree of similarity to the initial pattern.

In Example 27, the method according to any one of Examples 19-26, wherein the characteristic representation of sensed activation across the plurality of electrodes is a vector field consisting of a plurality of vectors each denoting a direction and magnitude of propagation at each electrode location.

In Example 28, the method according to any one of Examples 19-27, wherein the initial pattern template consists of at least one pattern based on focal activity located at various regions covered by the plurality of electrodes and one pattern based on rotor activity at various regions covered by the plurality of electrodes.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
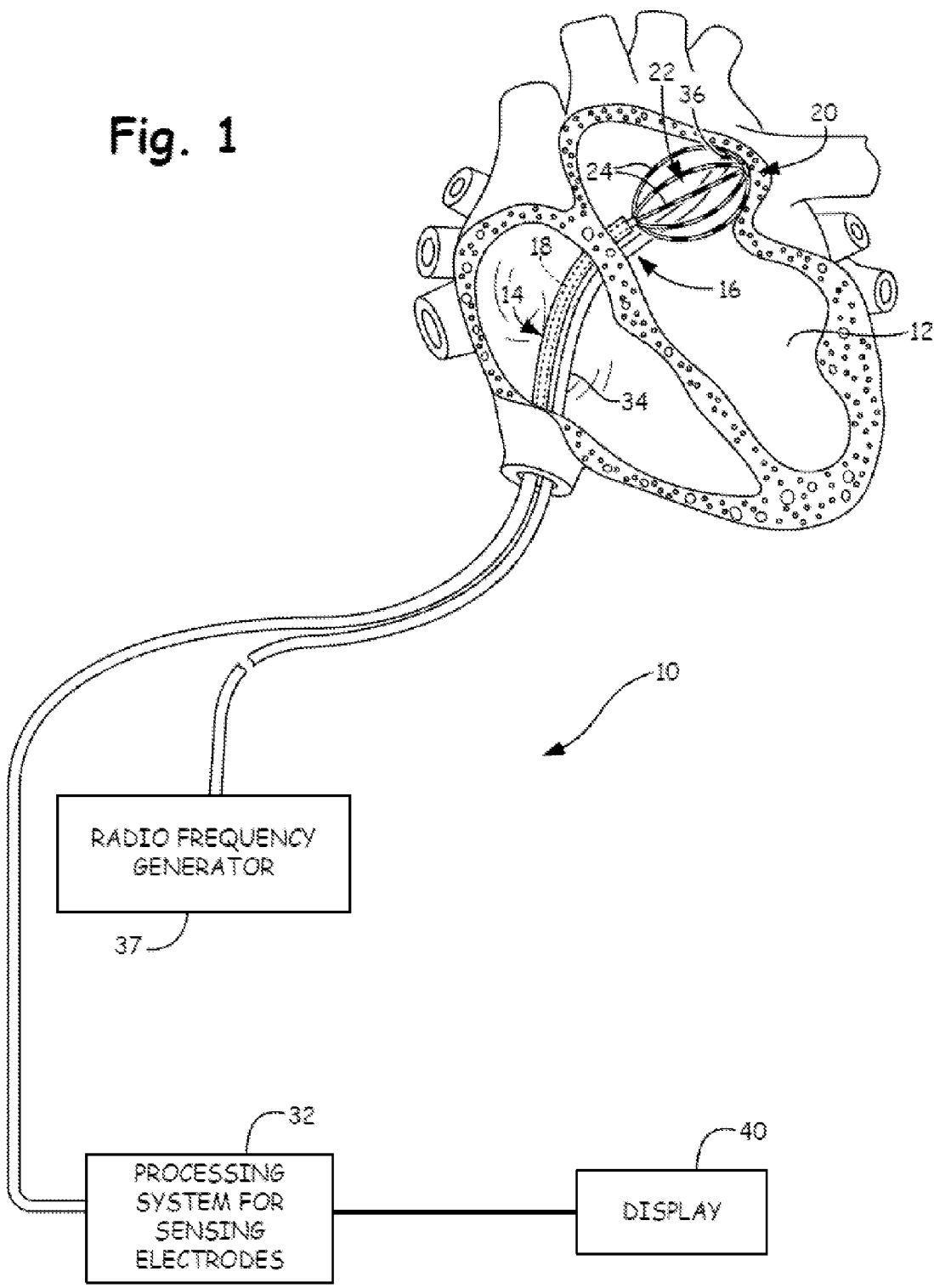
FIG. 1 is a schematic view of an embodiment of a system for accessing a targeted tissue region in the body for diagnostic and therapeutic purposes.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a system 10 for accessing a targeted tissue region in the body for diagnostic or therapeutic purposes. FIG. 1 generally shows the system 10 deployed in the left ventricle of the heart. Alternatively, system 10 can be deployed in other regions of the heart, such as the left atrium, right atrium, or right ventricle. While the illustrated embodiment shows the system 10 being used for ablating myocardial tissue, the system 10 (and the methods described herein) may alternatively be configured for use in other tissue ablation applications, such as procedures for ablating tissue in the prostrate, brain, gall bladder, uterus, and other regions of the body, including in systems that are not necessarily catheter-based.

The system 10 includes a mapping probe 14 and an ablation probe 16. In FIG. 1, each is separately introduced into the selected heart region 12 through a vein or artery (e.g., the femoral vein or artery) through suitable percutaneous access. Alternatively, the mapping probe 14 and ablation probe 16 can be assembled in an integrated structure for simultaneous introduction and deployment in the heart region 12.

The mapping probe 14 has a flexible catheter body 18. The distal end of the catheter body 18 carries a three-dimensional multiple electrode structure 20. In the illustrated embodiment, the structure 20 takes the form of a basket defining an open interior space 22 (see FIG. 2), although other multiple electrode structures could be used wherein the geometry of the electrode structure and electrode locations are known. The multiple electrode structure 20 carries a plurality of mapping electrodes 24 each having an electrode location and channel. Each electrode 24 is configured to sense intrinsic physiological activity in the anatomical region on which the ablation procedure is to be performed. In some embodiments, the electrodes 24 are configured to detect activation signals of the intrinsic physiological activity within the anatomical structure, e.g., the activation times of cardiac activity.

The electrodes 24 are electrically coupled to a processing system 32. A signal wire (not shown) is electrically coupled to each electrode 24 on the basket structure 20. The wires extend through the body 18 of the probe 14 and electrically couple each electrode 24 to an input of the processing system 32, as will be described later in greater detail. The electrodes 24 sense intrinsic electrical activity in the anatomical region, e.g., myocardial tissue. The sensed activity, e.g. activation signals, is processed by the processing system 32 to assist the physician by generating an anatomical map, e.g., a vector field map, to identify the site or sites within the heart appropriate for ablation. The processing system 32 identifies a near-field signal component, i.e. activation signals associated with local activation and originating from the tissue adjacent to the mapping electrode 24, from an obstructive far-field signal component, i.e. activation signals originating from non-adjacent tissue, within the sensed activation signals. For example, in an atrial study, the near-field signal component includes activation signals originating from atrial myocardial tissue whereas the far-field signal component includes activation signals originating from the ventricular myocardial tissue. The near-field activation signal component can be further analyzed to find the presence of a pathology and to determine a location suitable for ablation for treatment of the pathology, e.g., ablation therapy.

The processing system 32 includes dedicated circuitry (e.g., discrete logic elements and one or more microcontrollers; application-specific integrated circuits (ASICs); or specially configured programmable devices, such as, for example, programmable logic devices (PLDs) or field programmable gate arrays (FPGAs)) for receiving and/or processing the acquired activation signals. In some embodiments, the processing system 32 includes a general purpose microprocessor and/or a specialized microprocessor (e.g., a digital signal processor, or DSP, which may be optimized for processing activation signals) that executes instructions to receive, analyze and display information associated with the received activation signals. In such implementations, the processing system 32 can include program instructions, which when executed, perform part of the signal processing. Program instructions can include, for example, firmware, microcode or application code that is executed by microprocessors or microcontrollers. The above-mentioned implementations are merely exemplary, and the reader will appreciate that the processing system 32 can take any suitable form.

In some embodiments, the processing system 32 may be configured to measure the intrinsic electrical activity in the myocardial tissue adjacent to the electrodes 24. For example, in some embodiments, the processing system 32 is configured to detect intrinsic electrical activity associated with a dominant rotor or divergent activation pattern in the anatomical feature being mapped. Studies have shown that dominant rotors and/or divergent activation patterns have a role in the initiation and maintenance of atrial fibrillation, and ablation of the rotor path, rotor core, and/or divergent foci may be effective in terminating the atrial fibrillation. In either situation, the processing system 32 processes the sensed activation signals to generate a display of relevant characteristic, such as an APD map, a vector field map, a contour map, a reliability map, an electrogram, and the like. The relevant characteristics may be used by the physician to identify a site suitable for ablation therapy.

The ablation probe 16 includes a flexible catheter body 34 that carries one or more ablation electrodes 36. The one or more ablation electrodes 36 are electrically connected to a radio frequency generator (RF) 37 that is configured to deliver ablation energy to the one or more ablation electrodes 36. The ablation probe 16 is movable with respect to the anatomical feature to be treated, as well as the structure 20. The ablation probe 16 is positionable between or adjacent to electrodes 24 of the structure 20 as the one or more ablation electrodes 36 are positioned with respect to the tissue to be treated.

The processing system 32 outputs to a device 40 the display of relevant characteristics for viewing by a physician. In the illustrated embodiment, device 40 is a CRT, LED, or other type of display, or a printer). The device 40 presents the relevant characteristics in a format most useful to the physician. In addition, the processing system 32 may generate position-identifying output for display on the device 40 that aids the physician in guiding the ablation electrode(s) 36 into contact with tissue at the site identified for ablation.

Figure 2:
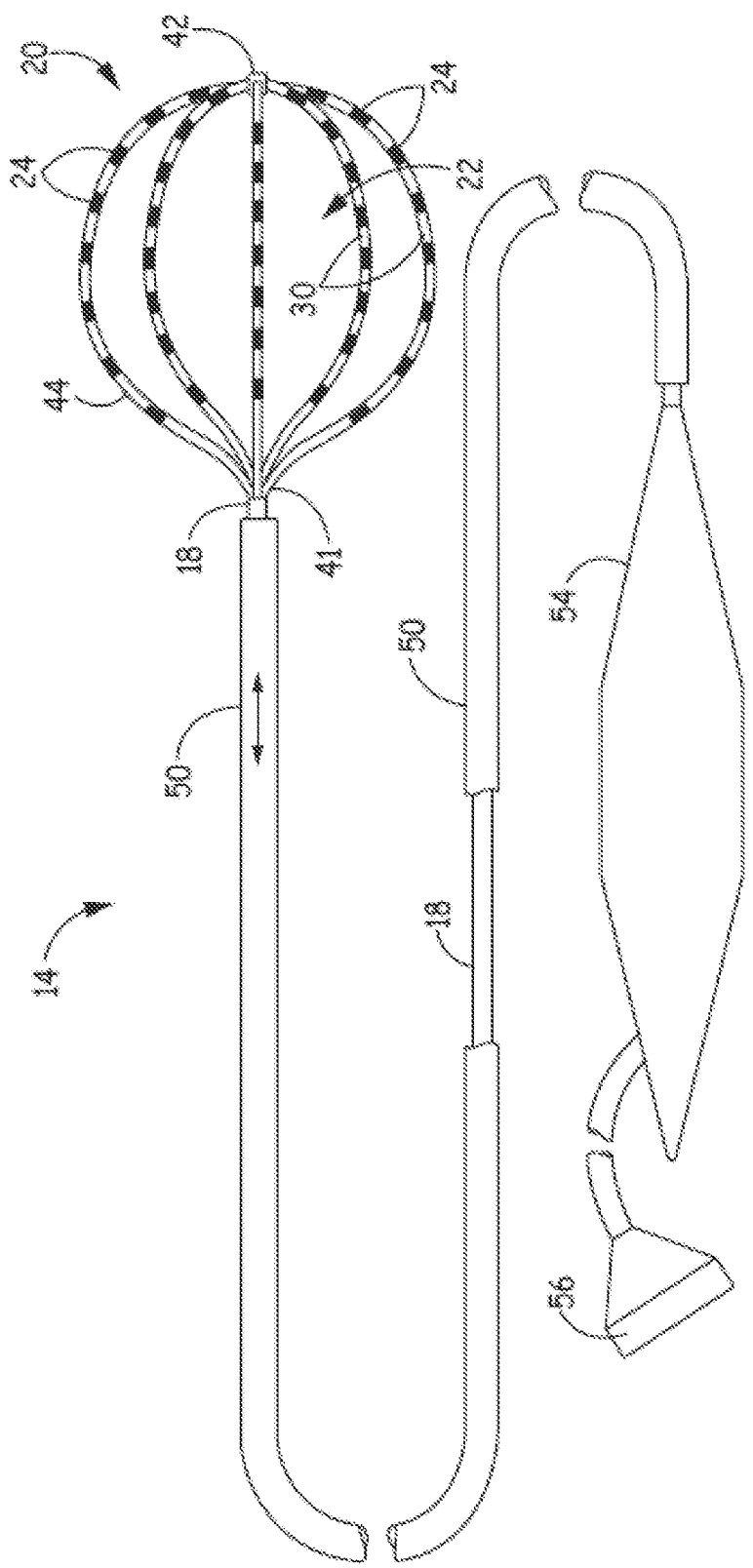
FIG. 2 is a schematic view of an embodiment of a mapping catheter having a basket functional element carrying structure for use in association with the system of FIG. 1.

FIG. 2 illustrates an embodiment of the mapping catheter 14 including electrodes 24 at the distal end suitable for use in the system 10 shown in FIG. 1. The mapping catheter 14 has a flexible catheter body 18, the distal end of which carries the three dimensional structure 20 configured to carry the mapping electrodes or sensors 24. The mapping electrodes 24 sense intrinsic electrical activity, e.g., activation signals, in the myocardial tissue, the sensed activity is then processed by the processing system 32 to assist the physician in identifying the site or sites having a heart rhythm disorder or other myocardial pathology via a generated and displayed relevant characteristics. This information can then be used to determine an appropriate location for applying appropriate therapy, such as ablation, to the identified sites, and to navigate the one or more ablation electrodes 36 to the identified sites.

The illustrated three-dimensional structure 20 comprises a base member 41 and an end cap 42 between which flexible splines 44 generally extend in a circumferentially spaced relationship. As discussed above, the three dimensional structure 20 takes the form of a basket defining an open interior space 22. In some embodiments, the splines 44 are made of a resilient inert material, such as Nitinol metal or silicone rubber, and are connected between the base member 41 and the end cap 42 in a resilient, pretensed condition, to bend and conform to the tissue surface they contact. In the illustrated embodiment, eight splines 44 form the three dimensional structure 20. Additional or fewer splines 44 could be used in other embodiments. As illustrated, each spline 44 carries eight mapping electrodes 24. Additional or fewer mapping electrodes 24 could be disposed on each spline 44 in other embodiments of the three dimensional structure 20. In the illustrated embodiment, the three dimensional structure 20 is relatively small (e.g., 40 mm or less in diameter). In alternative embodiments, the three dimensional structure 20 is even smaller or larger (e.g., 40 mm in diameter or greater).

A slidable sheath 50 is movable along the major axis of the catheter body 18. Moving the sheath 50 forward (i.e., toward the distal end) causes the sheath 50 to move over the three dimensional structure 20, thereby collapsing the structure 20 into a compact, low profile condition suitable for introduction into and/or removal from an interior space of an anatomical structure, such as, for example, the heart. In contrast, moving the sheath 50 rearward (i.e., toward the proximal end) exposes the three dimensional structure 20, allowing the structure 20 to elastically expand and assume the pretensed position illustrated in FIG. 2. Further details of embodiments of the three dimensional structure 20 are disclosed in U.S. Pat. No. 5,647,870, entitled "Multiple Electrode Support Structures," which is hereby expressly incorporated herein by reference in its entirety.

A signal wire (not shown) is electrically coupled to each mapping electrode 24. The wires extend through the body 18 of the mapping catheter 20 into a handle 54, in which they are coupled to an external connector 56, which may be a multiple pin connector. The connector 56 electrically couples the mapping electrodes 24 to the processing system 32. Further details on mapping systems and methods for processing signals generated by the mapping catheter are discussed in U.S. Pat. No. 6,070,094, entitled "Systems and Methods for Guiding Movable Electrode Elements within Multiple-Electrode Structure," U.S. Pat. No. 6,233,491, entitled "Cardiac Mapping and Ablation Systems," and U.S. Pat. No. 6,735,465, entitled "Systems and Processes for Refining a Registered Map of a Body Cavity," the disclosures of which are hereby expressly incorporated herein by reference.

It is noted that other multi-electrode structures could be deployed on the distal end of the mapping catheter 14. It is further noted that the multiple mapping electrodes 24 may be disposed on more than one structure rather than, for example, the single mapping catheter 14 illustrated in FIG. 2. For example, if mapping within the left atrium with multiple mapping structures, an arrangement comprising a coronary sinus catheter carrying multiple mapping electrodes and a basket catheter carrying multiple mapping electrodes positioned in the left atrium may be used. As another example, if mapping within the right atrium with multiple mapping structures, an arrangement comprising a decapolar catheter carrying multiple mapping electrodes for positioning in the coronary sinus, and a loop catheter carrying multiple mapping electrodes for positioning around the tricuspid annulus may be used.

Although the mapping electrodes 24 have been described as being carried by dedicated mapping probes, such as the mapping catheter 14, the mapping electrodes may be carried on non-mapping dedicated probes or multifunction probes. For example, an ablation catheter, such as the ablation catheter 16, can be configured to include one or more mapping electrodes 24 disposed on the distal end of the catheter body and coupled to the signal processing system 32 and guidance system (not shown). As another example, the ablation electrode at the distal end of the ablation catheter may be coupled to the signal processing system 32 to also operate as a mapping electrode.

Figure 3:
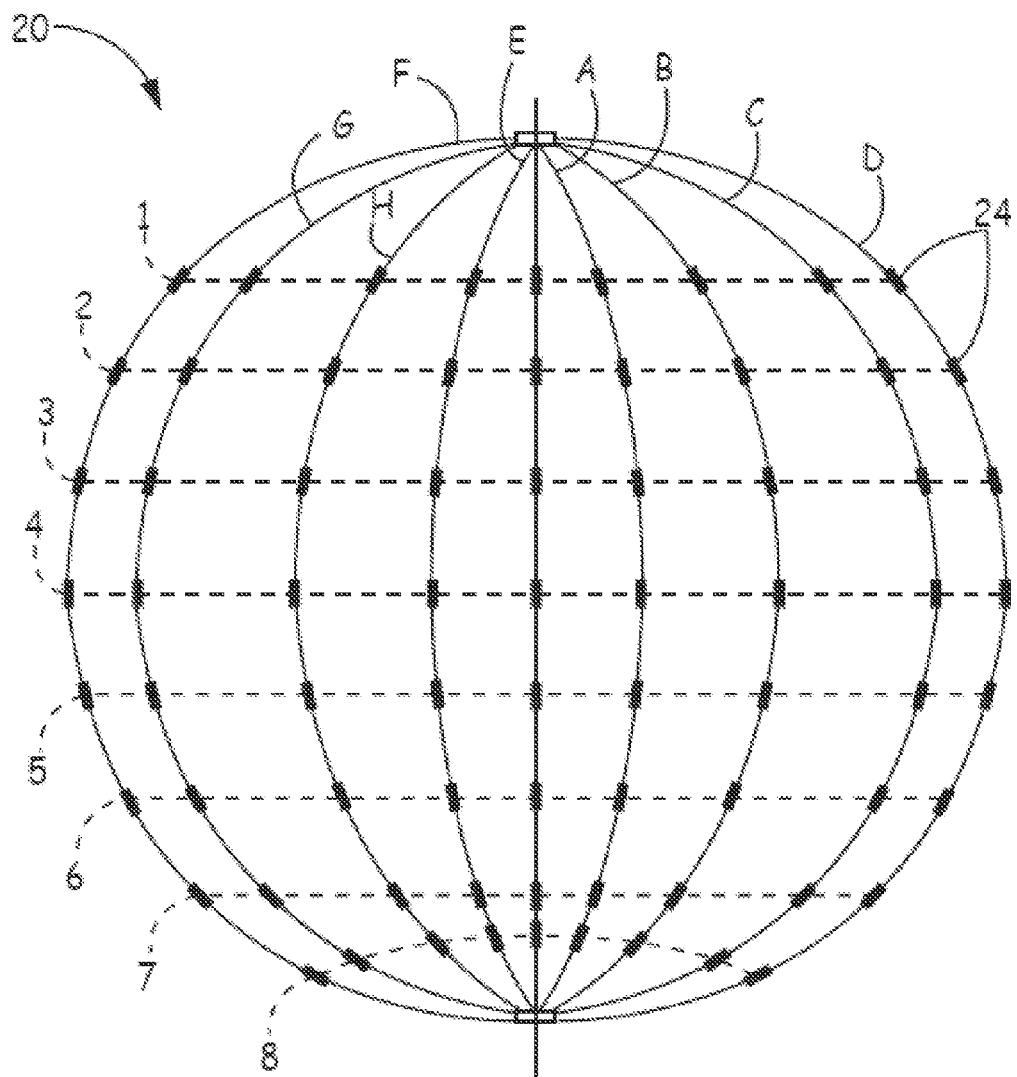
FIG. 3 is a schematic side view of an embodiment of the basket functional element including a plurality of mapping electrodes.

To illustrate the operation of the system 10, FIG. 3 is a schematic side view of an embodiment of the basket structure 20 including a plurality of mapping electrodes 24. In the illustrated embodiment, the basket structure includes 64 mapping electrodes 24. The mapping electrodes 24 are disposed in groups of eight electrodes (labeled 1, 2, 3, 4, 5, 6, 7, and 8) on each of eight splines (labeled A, B, C, D, E, F, G, and H) to a form an 8×8 array of electrodes 24. While an arrangement of sixty-four mapping electrodes 24 is shown disposed on a basket structure 20, the mapping electrodes 24 may alternatively be arranged in different numbers such as an M×N array (N electrodes each on M splines) of electrodes 24, on different structures, and/or in different positions. In addition, multiple basket structures can be deployed in the same or different anatomical structures to simultaneously obtain signals from different anatomical structures.

After the basket structure 20 is positioned adjacent to the anatomical structure to be treated, for example directly adjacent to or in direct contact with the interior of the left atrium or left ventricle of the heart, the processing system 32 is configured to record the activation signals from each electrode 24 channel related to intrinsic physiological activity of the anatomical structure, i.e. the electrodes 24 measure electrical activation signals intrinsic to the physiology of the anatomical structure.

In some embodiments, the processing system 32 is configured to identify dislocated and/or misplaced onset times for each sensed activation signal. An overlaying artifact signal, e.g. a far-field activation signals, or noise can cause a detected onset time for a true underlying local activation signal to be corrupted. After the activation signals of intrinsic physiological activity are sensed by the mapping electrodes 24, the processing system 32 generates a characteristic representation of a propagation pattern of the sensed electrical activity as the electrical signals propagate throughout tissue of the anatomical structure, e.g. left atrium or ventricle, during each heart beat. Characteristic representations can be generated individually for each beat, or averaged over multiple neighboring or subsequent beats. In one example, the characteristic representation can be a vector field over the M×N electrode array (N electrodes each on M splines). The vector field consists of a vector at each of the M×N electrode that indicates the direction of activity propagation at each of the M×N electrodes. In another example, the characteristic representation can be a contour map of activity propagation over the M×N electrode array during each heart beat. In yet another example, the characteristic representation could be the spatio-temporal evolution of the activity across the M×N electrodes denoted by a voltage map, Action potential duration map (APD) or a phase map over T time steps surrounding each beat.

In some embodiments the characteristic representation is a vector field. The vector field is a characteristic representation with a grid of vectors corresponding to each mapping electrode 24 location wherein each vector represents a local direction of propagation and magnitude of the activation signals sensed at the corresponding electrode 24 with respect to an adjacent or neighboring electrode 24 during a time period. The processing system 32 senses the activation signals at an electrode location and determines an onset time associated with the activation signal at the current electrode location. To determine the vector corresponding to the propagating activation signal, the processing system 32 calculates a circular average of detected activation signals at adjacent or neighboring electrodes 24 according to latency between an activation signal onset time at a current electrode location and an activation signal onset time at a neighboring electrode location. This is repeated for all mapping electrodes 24 for all electrode locations until the grid of vectors corresponding to each electrode 24 is generated.

The onset time is the time or a timestamp the processing system 32 assigns to the detection or sensing of the commencement of electrical activity associated with the activation signals arriving at an electrode location. The electrodes 24 of the M×N array detect the propagation of the activation signals during a heartbeat, i.e. electrical signals associated with an action potential depolarization or the cardiac tissue cells. The processing system 32 determines the onset times based on a derivative of each activation signal. The derivative detects changes in amplitude of the activation signals, e.g. a heart beat elicits a sharp rise in amplitude within sensed electrical signal in the heart. The processing system identifies minimum peaks among the derivative activation signals. The minimum peaks can be identified as onset times. As previously noted, far-field activation signals and noise, among other artifacts, can cause an inappropriately identified onset time. For example, multiple large minimum peaks in close proximity to or artifact signals overlying the signal of interest can cause ambiguities when determining onset times such as dislocated and confounded minimum peaks in the derivative signal. The processing system 32 generates an initial characteristic representation, for example an initial vector field, based on determined initial onset times, i.e. onset times determined based on the sensed activation signals.

In some embodiments, the processing system is further configured to identify alternative onset time candidates. The onset time candidates can be onset times identified within a local neighborhood directly before and after the determined onset time or initial onset time. The local neighborhood can include time window that surrounds the initial onset time. The processing system can identify other minimum peaks that fall within the surrounding onset time window. If necessary, the processing system can limit those onset time candidates that fall within in the onset time window based on their amplitude and/or the amplitude of the initial onset time. For example, if the amplitude of the onset time candidate is within a percentage of the corresponding initial onset time, the processing system will limit the identified onset time candidates as those falling within the amplitude percentage threshold. Other thresholds are also contemplated, such as fixed amplitude threshold rather than a percentage based threshold.

The processing system 32 is configured to determine or identify an initial pattern template from a bank of pattern templates which most closely matches the initial characteristic representation, wherein each pattern template is representative of characteristic propagation patterns that have been observed in the past or expected to occur. In the example where the characteristic pattern is a vector field, the bank of pattern templates can include a plurality of characteristic propagation patterns such as various curl patterns, divergent patterns, laminar patterns, and the that are centered or oriented at various locations and at various angles within the vector field. Similar propagation patterns can be used for other characteristic representation such that the template patterns are corresponding representative propagation patterns, e.g. contour map, a voltage map, an APD map, a phase map, or the like. To determine the initial pattern template, the processing system 32 compares the generated initial vector field (the vector field generated based on initial onset times) with each pattern template vector field stored in the bank of pattern template vector fields. The pattern templates can be normalized according to, for example, a Frobenius norm to yield ideal vector fields which are represented in terms of units vectors and compared to each characteristic representation based on the described methods.

The comparison can yield a similarity index or degree of similarity based upon the similarity or dissimilarity between the initial vector field or initial characteristic representation and the pattern templates compared therewith. The pattern template with the highest degree of similarity is identified as the initial pattern template or signature pattern template and the corresponding similarity index is identified as the initial similarity index. Therefore, the processing system 32 can determine initial onset times along with candidate onset times and can generate an initial characteristic representation from which an initial template pattern and corresponding initial similarity index is identified.

The bank of pattern templates can be a database or an array or a plurality of pattern templates that are stored locally in memory in the processing system 32 or can be stored in a remote location and accessed via a network or internet connection. Each pattern template represents a priori expected patterns of interest (e.g. a curl, a divergent, or a laminar pattern) and a location, direction, and/or angle associated with each pattern. In one example, a pattern template may be related to identifying a dominant rotor and/or divergent activation pattern associated with cardiac fibrillation. Each pattern template may represent a unique pattern having a unique location wherein patterns include, for example, a curled pattern which can represent rotor activity including a rotor core and/or rotor path having a core location or a divergent pattern representing focal activity having a foci location. The pattern templates can represent a vector field, contour map, a time dependent voltage map or phase map, an action potential duration map, or any characteristic representation that can be utilized to represent the sensed activation signals and/or electrical activity as they propagation through the anatomical structure of interest.

To identify which onset time, either the initial onset time or one of the alternative onset time candidates, is the accurate onset time of the corresponding activation signal, the processing system 32 iteratively replaces the initial onset times with the corresponding alternative onset time candidates and generates a candidate characteristic representation for each iteration, i.e. for each onset time candidate a candidate characteristic representation is generated. Each candidate characteristic representation is compared to the initial pattern template and a degree of similarity determined therebetween. If the degree similarity between the candidate characteristic representation and the initial template pattern is greater than the degree of similarity between the initial characteristic pattern and the initial template pattern, the initial characteristic representation is updated with the onset time candidate that corresponds to the candidate characteristic representation which has a similarity index greater than the initial similarity index. Therefore, the processing system 32 determines an optimized onset for each activation signal time based on the comparison between the candidate characteristic representation and the initial pattern template.

In the example of vector field characteristic representation, the processing system 32 iteratively replaces an initial onset time with the corresponding onset time candidates and generates a candidate vector field based on that onset time candidate. Each candidate vector field is compared to the initial pattern template and a similarity index is determined. If the current similarity index is greater than the initial similarity index, the initial onset time is updated or replaced with candidate onset time and the initial vector field is updated with the new initial onset time. Furthermore, the initial similarity index is updated or replaced by the current similarity vector. The processing system 32 repeats the method for each onset time candidate until an optimized onset time is determined for each initial onset time. It should be noted that the initial onset time can be the optimized onset time for an activation signal if the onset time candidates do not manifest a similarity index greater than the initial similarity index.

In some embodiments, comparing the determined characteristic representations to the pre-determined template patterns may not be suitable or appropriate as they may artificially bias the sensed activation signals and ensuing characteristic representations towards a priori expectations of the user. Alternatively, the processing system 32 can average a selected number of generated initial characteristic representations and use the resulting averaged characteristic representation as a pattern template. In this case, the pattern templates are data driven and unique to each subject and/or set of sensed activations signals. Determining the initial pattern template based on the activation signals sensed from the subject avoids the risk of artificially imposing a pattern due to a priori expectations or beliefs when using a bank of pattern templates that can generated from other subjects or ideal circumstances. The user or physician can select a number of preceding or proceeding characteristic representations adjacent to the initial characteristic representation as candidates to be averaged and represented as the initial pattern template.

The comparison between an initial characteristic representation and pattern template can be done via a number of similarity determination methods which determine a degree of similarity therebetween. For example, a similarity index could be generated via a cross-correlation measure. In another example, each characteristic representation can be treated as a single vector, i.e. a super-vector, wherein standard vector comparison methods from linear algebra can be used to derive a similarity index or measure. For example, a vector field over M×N electrodes can be treated as a super-vector in an M×N×2 dimensional space. Alternatively, a spatio-temporal characteristic representation over T time-steps, such as an APD map, voltage map, or phase map, can also be treated as a super-vector in an MnN×T dimensional space.

The processing system 32 determines a projection of a super-vector derived from each initial characteristic representations onto a super-vector derived from each pattern template. The processing system 32 determines a projection energy from the projection of super-vectors which can be used as a measure or index of similarity. The similarity index calculation can be based on a similarity algorithm that ranks the pattern templates in terms of similarity towards the corresponding initial pattern template. Other algorithms to identify the pattern template which represents the initial characteristic representation most accurately can include any one of a dissimilarity algorithm, a correlation algorithm, a distance algorithm, an object detection algorithm, an image processing, any combination thereof, and the like. After the pattern template with the maximum or optimal degree of similarity is determined, the processing system 32 identifies the corresponding projection as an initial projection. The initial projection is noted as the initial similarity index and can be used to determine which one set time is the most accurate onset time to associate with the sensed activation signal.

Returning to the vector field example, the processing system 32 iteratively replaces each onset time with one of the alternative onset time candidates. A new candidate vector field characteristic representation is generated during each iteration and is then compared to the identified pattern template and thus a current similarity index is also determined during each iteration. Each current similarity index is compared to the initial similarity index which was used to identify the initial pattern template. If a current index exceeds the initial index in similarity, then the initial vector field characteristic representation is updated with the onset time candidate that corresponds to the vector field that was generated based on the onset time candidate. Furthermore, the current similarity index now replaces the initial similarity index, and is now used as the initial similarity index for subsequent iterations. Therefore, the initial vector field characteristic representation is iteratively updated with the most accurate or optimized onset time, i.e. the first determined or initial onset time or one of the alternative onset time candidates. Once all of the onset time candidates have been exhausted, the resultant vector field characteristic representation will be updated with the most accurate or optimized onset time for each sensed activation signal at each electrode location.

In some embodiments, the identified initial pattern template can be held constant over all subsequent iterations. Alternately, it is also contemplated that after every iteration a new initial pattern template is identified based on the updated onset times and the optimized initial characteristic pattern after the completion of each iteration. In this embodiment, the processing system could potentially discover a different or initial pattern template even though the initial onset times and the initial vector field characteristic representation are biased to a completely different pattern template. Therefore, the initial pattern template does not remain static; rather it is dynamically updated or optimized with each iteration.

In some embodiments, the processing system 32 computes angles or distances between corresponding super-vectors of the initial and/or current characteristic representations and pattern templates to determine which onset time is the most accurate onset time. If a current angle or current distance is less than an initial angle or initial distance, respectively, the processing system updates the initial onset time with the corresponding current onset time.

In some embodiments, the processing system is further configured to identify dislocated or misplaced onset times. An overlaying artifact signals (e.g. far-field activation signal) or noise can cause a peak in the derivative signal to be identified at a different temporal location. After identifying the onset times and alternative onset time candidates a previously described, the processing system 32 identifies activation signals with no alternative onset time candidates associated with the lone determined initial onset time, i.e. solitary onset times. In one embodiment, the initial vector field characteristic representation is generated for each activation signal based on the determined initial onsite times. An initial pattern template for each initial vector field is identified along with a corresponding initial similarity index as previously described. The processing system iteratively removes each solitary onset time and generates a current vector field during each iteration. A current similarity index is determined based on a comparison of each current vector field onto the initial vector field. Each current similarity index is compared to the initial similarity index which was used to identify to the initial pattern template. If a current similarity index exceeds the initial similarity index, then the initial vector field is updated without the corresponding solitary onset time. Therefore, the initial vector field is iteratively updated with solitary onset times removed if they do not accurately correspond to an activation signal. Once all dislocated or misplaced solitary onset times have been iteratively removed, the resultant vector field will be updated or optimized with the most accurate onset time for each sensed activation signal at each electrode location.

Figure 4:
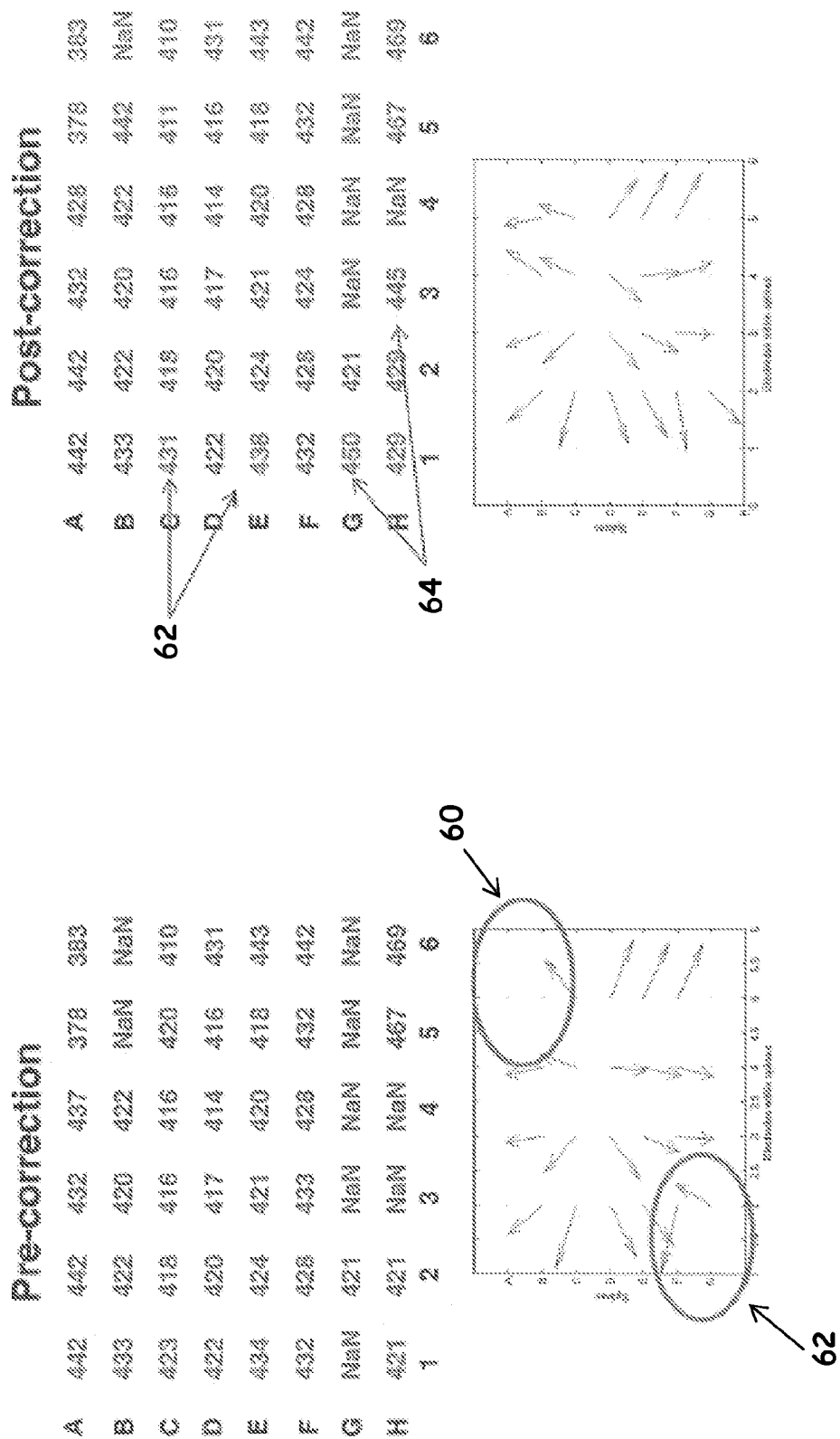
FIG. 4 is an illustration of an initial vector field and corresponding initial onset times before and after correction of the onset times.

FIG. 4 illustrates determined onset times prior to the correction of occluded or misplaced onset times. As shown by the circled regions 60, 62 in the initial vector field, some vectors are missing entirely 60 and some vectors are misplaced 62. In the post-correction onset times shown on the right, some onset times were changed 64 to reveal the most accurate onset time while some onset times 66 were recovered after the initial onset time was not identifiable.

Figure 5:
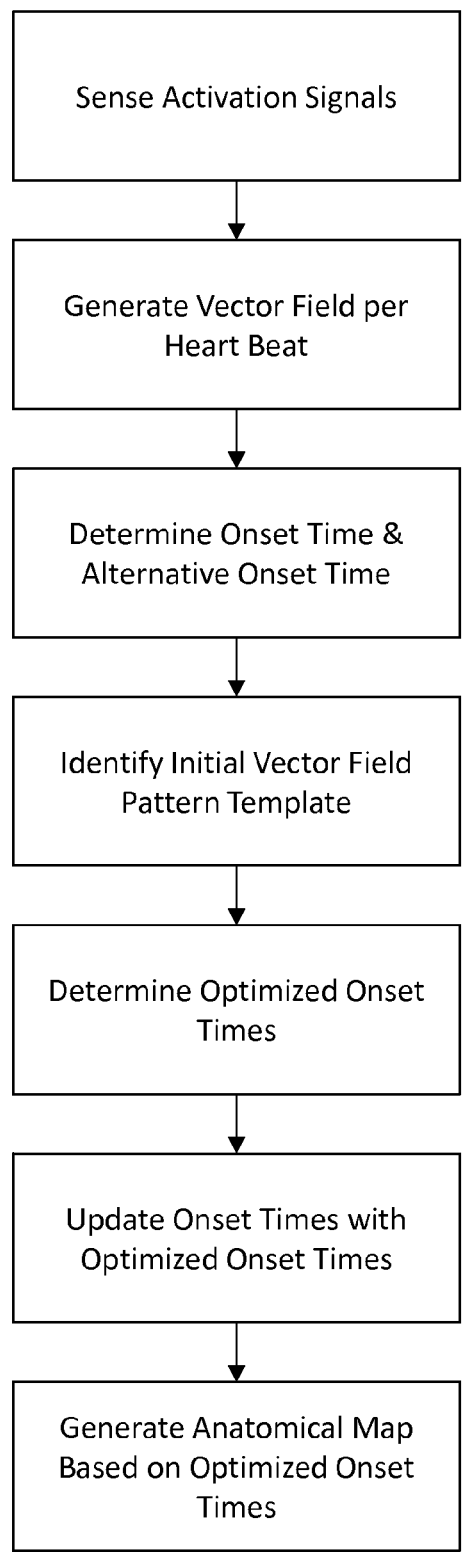
FIG. 5 is a method flow chart for mapping cardiac tissue.

FIG. 5 details a method for mapping cardiac tissue in vivo. After the mapping probe 14 is introduced into a cardiac chamber, the processing system 32 senses activation signals of electrical activity generated the cardiac tissue during each heart beat with the plurality of mapping electrodes 24 disposes at the distal end of the processing system 32. The processing system 32 generates a vector field of the sensed electrical activity or activation signals as they propagate throughout the cardiac tissue during each heart beat. For each activation signal, the processing system 32 determines and onset time according to peaks identified in a derivative signal of the corresponding activation signal. In the presence of noise in and around the heart, determined onset times may not be entirely accurate. Therefore, alternative onset time candidates are determined for each onset time. These candidates may be identified according to local peaks in and around the determined onset time.

A bank pattern templates that are representative of characteristic propagation patterns that have been observed in the past or expected to occur is used to identify an initial vector field pattern template. Each generated vector field is compared to each pattern template to determine a degree of similarity therebetween. The pattern template which most closely matches or has the highest degree of similarity is identified as the initial vector field pattern template corresponding to the vector field. The initial vector field pattern template can be used to determine an optimized onset time for each activation signal based on the corresponding onset time candidates and onset times associated with the identified initial vector field pattern template. If an optimized onset time is different than the initial onset time, the initial onset time is updated or replaced with the corresponding optimized onset time. The processing system 32 repeats this processes for each heart beat and the corresponding sensed activations corresponding to each heart beat. A vector field or anatomical map of the heart can be generated and displayed based on the optimized onset times.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method for mapping an anatomical structure, the method comprising:
sensing activation signals during an instance of physiological activity with a plurality of mapping electrodes disposed in or near the anatomical structure;
generating a vector field for each sensed activation signal during each instance of the physiological activity;
determining an onset time and alternative onset time candidates for each activation signal;
identifying an initial vector field pattern template for each activation signal based on a degree of similarity between the generated vector field and at least one vector field template pattern;
generating a vector field candidate for each onset time candidate;
identifying, for each activation signal, a vector field candidate that has a maximum similarity index with the initial vector field pattern template; and
determining an optimized onset time for each activation signal based on the identified vector field candidate.

2. The method according to claim 1, further comprising:
replacing the determined onset times with corresponding optimized onset times; and
generating a display on a display device of the activation signals based on the optimized onset times.

3. The method according to claim 1, wherein determining an onset time further includes:
calculating a derivative of the sensed activation signals; and
identifying a minimum peak for each sensed activation signal.

4. The method according to claim 3, wherein determining alternative onset time candidates further includes:
  identifying negative peaks among the derivative sensed activation signals which are at least one of within a local neighborhood of an identified minimum peak and within an amplitude threshold based on the amplitude of the corresponding minimum peak.

5. A method for mapping cardiac tissue, the method comprising:
  sensing activation signals of electrical cardiac activity during each heart beat with a plurality of mapping electrodes disposed in or near the heart;
  generating a vector field for each sensed activation signal during each heart beat;
  determining an onset time and alternative onset time candidates for each activation signal;
  identifying an initial vector field pattern template for each activation signal based on a degree of similarity between the generated vector field and at least one vector field template pattern;
  generating a vector field candidate for each onset time candidate;
  identifying, for each activation signal, a vector field candidate that has a maximum similarity index with the initial vector field pattern template; and
  determining an optimized onset time for each activation signal based on the identified vector field candidate.

6. The method according to claim 5, further comprising:
  replacing the determined onset times with corresponding optimized onset times; and
  generating a display on a display device of the activation signals of the heart based on the optimized onset times.

7. The method according to claim 5, wherein determining an onset time further includes:
  calculating a derivative of the sensed activation signals; and
  identifying a minimum peak for each sensed activation signal.

8. The method according to claim 7, wherein determining alternative onset time candidates further includes:
  identifying negative peaks among the derivative sensed activation signals which are at least one of within a local neighborhood of an identified minimum peak and within an amplitude threshold based on the amplitude of the corresponding minimum peak.

9. An anatomical mapping system comprising:
  a plurality of mapping electrodes disposed in or near the anatomical structure configured to detect activation signals during an instance of physiological activity;
  a processing system associated with the plurality of mapping electrodes, the mapping processor configured to record the detected activation signals and associate one of the plurality of mapping electrodes with each recorded activation signal, the processor system further configured to generate a vector field for each sensed activation signal during each instance of the physiological activity; determine an onset time and alternative onset time candidates for each activation signal; identify an initial vector field pattern template for each activation signal based on a degree of similarity between the generated vector field and at least one vector field template pattern; generate a vector field candidate for each onset time candidate; identify, for each activation signal, a vector field candidate that has a maximum similarity index with the initial vector field pattern template; and determine an optimized onset time for each activation signal based on the identified vector field candidate.

10. The anatomical mapping system according to claim 9, wherein the processing system is further configured to replace the determined onset times with corresponding optimized onset times, and generate a display on a display device of the activation signals based on the optimized onset times.

11. The anatomical mapping system according to claim 9, wherein, to determine an onset time, the processing system is further configured to calculate a derivative of the sensed activation signals, and identifying a minimum peak for each sensed activation signal.

12. The anatomical mapping system according to claim 11, wherein, to determine alternative onset time candidates, the processing system is further configured to identify negative peaks among the derivative sensed activation signals which are at least one of within a local neighborhood of an identified minimum peak and within an amplitude threshold based on the amplitude of the corresponding minimum peak.

13. A method for mapping an anatomical structure, the method comprising:
  sensing activation signals of physiological activity with a plurality of mapping electrodes disposed in or near the anatomical structure, each mapping electrode having an electrode location;
  determining an onset time and alternative onset time candidates for each activation signal, wherein an onset time indicates an onset of activation signals at a corresponding electrode location during the corresponding instance of the physiological activity;
  generating an initial characteristic representation of the sensed activation signals based on the determined onset times during the corresponding instance of physiological activity;
  determining an initial pattern for each initial characteristic representation, the initial pattern representing a characteristic propagation pattern of the activations signals during the corresponding instance of the physiological activity;
  generating a candidate characteristic representation of the sensed activation signal based on each of the corresponding alternative onset time candidates;
  determining an optimized onset time for each activation signal based on the candidate characteristic representation that has a maximum similarity index with the initial pattern.

14. The method according to claim 13, further comprising:
  replacing the determined onset times with corresponding optimized onset times; and
  generating a display of the activation pattern on a display device based on the optimized onset times.

15. The method according to claim 13, wherein determining an onset time further includes:
  calculating a derivative of the sensed activation signals; and
  identifying a minimum peak for each sensed activation signal.

16. The method according to claim 15, wherein determining alternative onset time candidates further includes:
  identifying negative peaks among the derivative sensed activation signals which are at least one of within a local neighborhood of an identified minimum peak and within an amplitude threshold based on the amplitude of the corresponding minimum peak.

17. The method according to claim 13, wherein determining an initial pattern further includes:
  determining a similarity index between the initial characteristic representation and each of a plurality of pattern templates of a bank of pattern templates; and identifying the pattern template which maximizes the degree of similarity to the initial characteristic representation.

18. The method according to claim 17, wherein and the pattern templates are characteristic representations of expected patterns of propagation across the plurality of electrodes.

19. The method according to claim 13, wherein the characteristic representation of sensed activation across the plurality of electrodes is a vector field consisting of a plurality of vectors each denoting a direction and magnitude of propagation at each electrode location.

20. The method according to claim 19, wherein the initial pattern template consists of at least one pattern based on focal activity located at various regions covered by the plurality of electrodes and one pattern based on rotor activity at various regions covered by the plurality of electrodes.

* * * * *